(12) United States Patent
Miyaishi et al.

(10) Patent No.: US 9,516,881 B2
(45) Date of Patent: Dec. 13, 2016

(54) COPPER-AND-TITANIUM-CONTAINING COMPOSITION AND PRODUCTION METHOD THEREFOR

(71) Applicant: SHOWA DENKO K.K., Minato-ku, Toyko (JP)

(72) Inventors: So Miyaishi, Toyama (JP); Yasushi Kuroda, Toyama (JP); Yasuhiro Hosogi, Toyama (JP); Ding Li, Toyama (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 14/000,507

(22) PCT Filed: Dec. 17, 2012

(86) PCT No.: PCT/JP2012/082706
§ 371 (c)(1),
(2) Date: Aug. 20, 2013

(87) PCT Pub. No.: WO2013/094572
PCT Pub. Date: Jun. 27, 2013

(65) Prior Publication Data
US 2014/0322353 A1    Oct. 30, 2014

(30) Foreign Application Priority Data

Dec. 22, 2011  (JP) ................................. 2011-281896
May 28, 2012   (JP) ................................. 2012-121345
Aug. 8, 2012   (JP) ................................. 2012-175788

(51) Int. Cl.
| | | |
|---|---|---|
| *A01N 59/16* | (2006.01) | |
| *B01J 27/122* | (2006.01) | |
| *A01N 59/20* | (2006.01) | |
| *B01J 21/06* | (2006.01) | |
| *B01J 23/72* | (2006.01) | |
| *B01J 37/03* | (2006.01) | |
| *B01J 35/00* | (2006.01) | |
| *A01N 55/02* | (2006.01) | |
| *A61L 9/01* | (2006.01) | |
| *B01J 27/055* | (2006.01) | |
| *B01J 27/135* | (2006.01) | |
| *B01J 27/25* | (2006.01) | |
| *B01J 31/38* | (2006.01) | |

(52) U.S. Cl.
CPC .............. *A01N 59/16* (2013.01); *A01N 55/02* (2013.01); *A01N 59/20* (2013.01); *A61L 9/01* (2013.01); *B01J 21/063* (2013.01); *B01J 23/72* (2013.01); *B01J 27/055* (2013.01); *B01J 27/122* (2013.01); *B01J 27/135* (2013.01); *B01J 27/25* (2013.01); *B01J 31/38* (2013.01); *B01J 35/004* (2013.01); *B01J 37/033* (2013.01)

(58) Field of Classification Search
CPC ........ A01N 59/20; A01N 25/12; A01N 59/16; A01N 55/02; B01J 27/055; B01J 35/004; B01J 21/063; B01J 23/72; B01J 27/122; B01J 27/135; B01J 27/25; B01J 31/38; B01J 37/033; A61L 9/01
See application file for complete search history.

(56) References Cited

U.S. PATENT DOCUMENTS

| | | |
|---|---|---|
| 2002/0160910 A1 | 10/2002 | Sanbayashi et al. |
| 2010/0040655 A1 | 2/2010 | Ren et al. |
| 2011/0045964 A1 | 2/2011 | Abe et al. |
| 2012/0135861 A1 | 5/2012 | Hashimoto et al. |

FOREIGN PATENT DOCUMENTS

| | | |
|---|---|---|
| EP | 1354854 A1 | 10/2003 |
| EP | 2633907 A1 | 9/2013 |
| JP | 2000-95976 A | 4/2000 |
| JP | 2006-232729 A | 9/2006 |
| JP | 2009-56348 A | 3/2009 |
| JP | 2010-168578 A | 8/2010 |
| JP | 4646210 B2 | 3/2011 |
| JP | 2011-153163 A | 8/2011 |
| JP | 2011-190192 A | 9/2011 |
| JP | 2012-016697 A | 1/2012 |
| RU | 2 288 189 C1 | 11/2006 |
| WO | 02/053501 A1 | 7/2002 |
| WO | 2011/068094 A1 | 6/2011 |

OTHER PUBLICATIONS

Suyasu, Y. et al. Antiviral agent, and antiviral agent functional product using same, WO 2011/068094, published: Sep. 6, 2011, English Machine Translation (Google), accessed online on Oct. 16, 2014.*
Yoshiaki, S. Photocatalyst dispersion, JP 2009/056348, published: Mar. 19, 2009, English Machine Translation (PAJ), accessed online on Oct. 16, 2014.*
C. Karunakaran et al., "Cu-doped TiO2 nanoparticles for photocatalytic disinfection of bacteria under visible light5", Journal of Colloid and Interface Science 2010, pp. 68-74, vol. 352.

(Continued)

*Primary Examiner* — Johann R Richter
*Assistant Examiner* — Genevieve S Alley
(74) *Attorney, Agent, or Firm* — Sughrue Mion, PLLC

(57) ABSTRACT

The Cu- and Ti-containing composition of the present invention contains titanium oxide having a rutile-type titanium oxide content of 15 mol % or more, and at least one divalent copper compound represented by the following formula (1). The Cu- and Ti-containing composition production method of the present invention is characterized by including stirring a mixture containing titanium oxide having a rutile-type titanium oxide content of 15 mol % or more, a divalent copper compound raw material represented by formula (2), water, and an alkaline compound, to thereby cause precipitation. The composition of the present invention exhibits excellent anti-viral property under light and in the dark, and excellent organic compound decomposition activity under light.

13 Claims, 1 Drawing Sheet

(56) References Cited

OTHER PUBLICATIONS

International Search Report for PCT/JP2012/082706 dated Jan. 29, 2013.
Communication dated Sep. 5, 2014, issued by the European Patent Office in corresponding Application No. 12860366.9.
European Communication pursuant to Article 94(3) EPC for Application No. 12 860411.3 1352, dated Nov. 18, 2015, 15 pages.

* cited by examiner

COPPER-AND-TITANIUM-CONTAINING COMPOSITION AND PRODUCTION METHOD THEREFOR

CROSS REFERENCE TO RELATED APPLICATIONS

This application is a National Stage of International Application No. PCT/JP2012/082706 filed Dec. 17, 2012, claiming priority based on Japanese Patent Application Nos. 2011-281896 filed Dec. 22, 2011, 2012-121345 filed May 28, 2012, and 2012-175788 filed Aug. 8, 2012, the contents of all which are incorporated herein by reference in their entirety.

TECHNICAL FIELD

The present invention relates to a copper- and titanium-containing composition containing rutile-type titanium oxide and a copper compound, to an anti-viral agent, to a photocatalyst, and to a method for producing a copper- and titanium-containing composition.

BACKGROUND ART

Photocatalysts employing titanium oxide are widely used by virtue of low price; high chemical stability, high photocatalytic activity (organic compound degradability, anti-bacterial property, etc.); non-toxicity to the human body; etc.

It has been known that a mixture of titanium oxide with metallic copper or a copper compound, or a product of titanium oxide on which copper or a copper compound has been deposited, serves as an excellent photocatalyst or an excellent anti-viral agent.

For example, Patent Document 1 discloses use of nano particles of a compound $M_nX_y$ for suppression and/or prevention of infection with viruses. Examples of the nano-particle compound include $TiO_2$, $Cu_2O$, CuO, and combinations thereof.

Regarding the aforementioned combinations of titanium oxide with metallic copper or a copper compound, particularly, the anti-viral performance of the photocatalysts has been enhanced by use of anatase-type titanium oxide.

For example, Patent Document 2 discloses an anti-bacterial photocatalytic aqueous coating material in which a metal such as copper is deposited on a photocatalyst such as titanium oxide. Patent Document 2 also discloses that titanium oxide preferably has an anatase-type crystal structure.

Patent Document 3 discloses a phage/virus inactivating agent formed of anatase-type titanium oxide containing copper at a $CuO/TiO_2$ (ratio by mass %) of 1.0 to 3.5. The invention of Patent Document 3 was accomplished with respect to the finding that copper-containing anatase-type titanium oxide can inactivate phages/viruses.

Regarding the aforementioned combinations of titanium oxide with metallic copper or a copper compound, it have been known that a monovalent copper compound has particularly used as a copper compound, and the monovalent copper exhibits excellent microorganism- and virus-inactivating performance.

For example, Patent Document 4 discloses an anti-viral coating material, characterized by containing a monovalent copper compound as an active ingredient which can inactivate viruses. Patent Document 4 also discloses that the monovalent copper compound inactivates a variety of viruses through contact therewith.

Patent Document 5 discloses a microorganism inactivating agent which contains a monovalent copper compound as an active ingredient for use in inactivation of microorganisms in a short time. Patent Document 5 also discloses another microorganism inactivating agent which contains a monovalent copper compound and a photocatalytic substance. The photocatalytic substance may be a titanium oxide catalyst. Patent Document 5 further discloses that a monovalent copper compound exhibits a remarkably strong microorganism-inactivating effect, as compared with a divalent copper compound.

Patent Document 1: Japanese Kohyo (PCT) Patent Publication No. 2009-526828
Patent Document 2: Japanese Patent Application Laid-Open (kokai) No. 2000-95976
Patent Document 3: Japanese Patent No. 4646210
Patent Document 4: Japanese Patent Application Laid-Open (kokai) No. 2010-168578
Patent Document 5: Japanese Patent Application Laid-Open (kokai) No. 2011-190192

Problems to be Solved by the Invention

Patent Document 1 discloses examples of the nano-particle form $M_nX_y$ for suppressing infection with viruses including $TiO_2$, $Cu_2O$, CuO, and combinations thereof. However, there has not been completely specified a member thereof which exhibits excellent anti-viral property under light and in the dark.

The phage/virus inactivating agent disclosed in Patent Document 2 exhibited the inactivating effect only under irradiation with UV rays, and there has not been completely specified which copper compound exhibits excellent anti-viral property under light and in the dark.

In Patent Document 3, $CuO/TiO_2$ samples were evaluated in terms of anti-viral effect under irradiation with UV rays (Examples 1 to 4, and Comparative Examples 3 and 4), under irradiation with visible light (Comparative Example 2), and in the dark (Comparative Example 1). Patent Document 3 discloses that "no phage inactivating effect was observed" in the dark (Comparative Example 1).

Virus-inactivating agents disclosed in Patent Documents 4 and 5 each contain a monovalent copper compound as an active ingredient which can inactivate a virus. However, monovalent copper compounds readily undergo oxidation, particularly when such a monovalent copper compound is pulverized to micro-particles (200 nm or less) for imparting transparency to an object containing the copper compound. When $Cu_2O$ (red) is oxidized to CuO (black), unevenness in color arises, thereby impairing the appearance of the object.

The present invention has been conceived under such circumstances. Thus, an object of the present invention is to provide a copper- and titanium-containing composition, which exhibits excellent anti-viral property under light and in the dark and excellent organic compound degradability under light. Hereinafter, the composition may be referred to also as "a Cu- and Ti-containing composition." Another object is to provide an anti-viral agent. Still another object is to provide a photocatalyst. Yet another object is to provide a method for producing such a Cu- and Ti-containing composition.

Means for Solving the Problems

As described above, the following is common general technical knowledge regarding anti-viral agents containing titanium oxide and a copper compound. That is, (i) use of anatase-type titanium oxide enhances anti-viral performance (Patent Documents 2 and 3), and (ii) a monovalent copper compound exhibits excellent anti-viral performance, but a divalent copper compound has no substantial anti-viral performance (Patent Documents 4 and 5).

However, in contrast to the common general technical knowledge, the present inventors have found that a specific divalent copper compound, which per se exhibits no substantial anti-viral performance, exhibits excellent anti-viral performance particularly when the divalent compound is used in combination with a specific titanium oxide (i.e., rutile-type titanium oxide). The present invention has been accomplished with respect to this finding.

Accordingly, the present invention provides the following [1] to [12].

[1] A Cu- and Ti-containing composition comprising titanium oxide having a rutile-type titanium oxide content of 15 mol % or more, and at least one divalent copper compound represented by the following formula (1):

$$Cu_2(OH)_3X \qquad (1)$$

(wherein X represents an anion).

[2] A Cu- and Ti-containing composition as described in [1] above, wherein, in formula (1), X is Cl.

[3] A Cu- and Ti-containing composition as described in [1] or [2] above, wherein the divalent copper compound represented by formula (1) has a copper content, as reduced to copper, of 0.01 to 10 parts by mass, with respect to 100 parts by mass of titanium oxide.

[4] A Cu- and Ti-containing composition as described in any of [1] to [3] above, wherein the titanium oxide has been produced through a vapor phase method.

[5] A Cu- and Ti-containing composition as described in any of [1] to [4] above, wherein the titanium oxide has a specific surface area of 8 to 50 m²/g.

[6] An anti-viral agent containing a composition as recited in any of [1] to [5] above.

[7] A photocatalyst containing a composition as recited in any of [1] to [5] above.

[8] A method for producing a Cu- and Ti-containing composition as recited in any of [1] to [5] above, characterized in that the method comprises stirring a mixture containing titanium oxide having a rutile-type titanium oxide content of 15 mol % or more, a divalent copper compound raw material represented by formula (2):

$$CuX_2 \qquad (2)$$

(wherein X represents an anion), water, and an alkaline compound, to thereby cause precipitation.

[9] A Cu- and Ti-containing composition production method as described in [8] above, wherein the mixture is stirred at a pH of 8 to 11.

[10] A Cu- and Ti-containing composition production method as described in [8] or [9] above, wherein the mixture has a titanium oxide concentration of 3 to 25 mass %.

[11] A Cu- and Ti-containing composition production method as described in any of [8] to [10] above, wherein, in formula (2), X is Cl.

[12] A virus inactivation method or a deodorization method, the method comprising inactivating a virus or deodorizing by use of a Cu- and Ti-containing composition as recited in any of [1] to [5] above.

Effects of the Invention

The present invention enables provision of a Cu- and Ti-containing composition, which exhibits excellent anti-viral property under light and in the dark and excellent organic compound degradability under light, an anti-viral agent, a photocatalyst, and a method for producing such a Cu- and Ti-containing composition.

MODES FOR CARRYING OUT THE INVENTION

[Cu- and Ti-Containing Composition]

Figure 1:
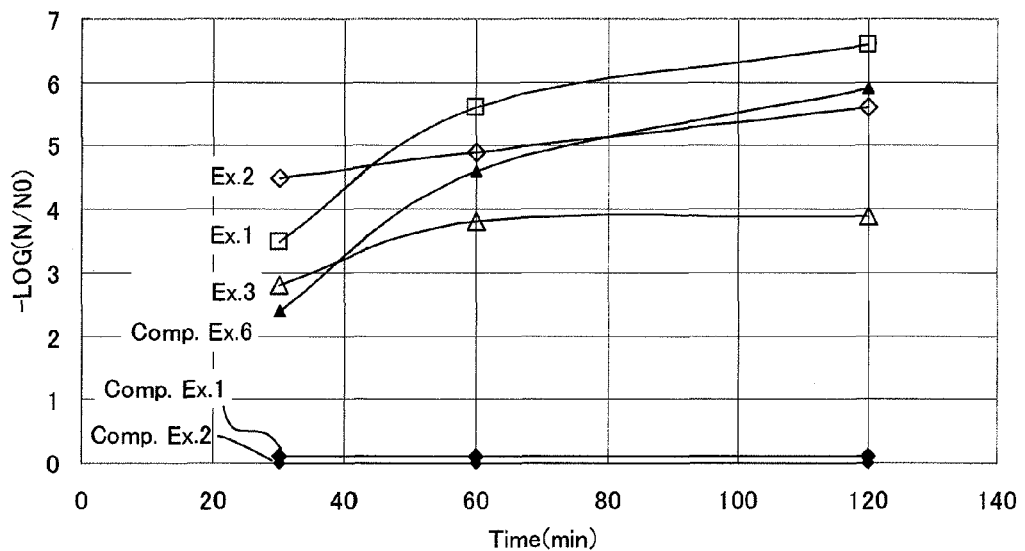
FIG. 1 A graph showing changes over time in relative phage concentration (LOG(N/N₀)) of samples of Examples 1 to 3 and Comparative Examples 1, 2, and 6, under light.

The Cu- and Ti-containing composition of the present invention contains titanium oxide having a rutile-type titanium oxide content of 15 mol % or more, and at least one divalent copper compound represented by the following formula (1):

$$Cu_2(OH)_3X \qquad (1)$$

(wherein X represents an anion).

Through use, in combination, of the aforementioned titanium oxide, and the divalent copper compound represented by formula (1), the produced Cu- and Ti-containing composition containing them exhibits excellent anti-viral property under light and in the dark and excellent organic compound degradability under light, particularly organic compound degradability under visible light (hereinafter may be referred to as "visible-light-response").

As used herein, the expression "X represents an anion" refers to that X is a chemical species which formed a corresponding anion when dissociated.

<Titanium Oxide>

The titanium oxide employed in the present invention is required to have a rutile-type titanium oxide content (hereinafter may be referred to as "rutile ratio") of 15 mol % or more. When the rutile-type titanium oxide content is less than 15 mol %, the produced Cu- and Ti-containing composition exhibits poor anti-viral property under light and in the dark, and organic compound degradability under light, in particular visible-light-response, is insufficient.

From the above viewpoint, the rutile-type titanium oxide content of titanium oxide is preferably 18 mol % or more, more preferably 50 mol % or more, still more preferably 90 mol % or more. As described hereinbelow, the rutile-type titanium oxide content (rutile ratio) is determined through XRD.

The titanium oxide preferably has a specific surface area of 1 to 200 m²/g. When the specific surface area is 1 m²/g or more, photocatalytic activity is enhanced by virtue of such a large specific surface area. In this case, the thus-produced Cu- and Ti-containing composition exhibits excellent anti-viral property under light and in the dark, excellent organic compound degradability, and excellent anti-bacterial property. When the specific surface area is 200 m²/g or less, handling of the composition is very easy. From these viewpoints, the specific surface area of titanium oxide is more preferably 3 to 100 m²/g, still more preferably 4 to 70 m²/g, particularly preferably 8 to 50 m²/g. The specific surface area is determined through the BET method employing nitrogen adsorption.

Preferably, titanium oxide is produced through a vapor phase method (i.e., production of titanium oxide through vapor phase reaction between titanium tetrachloride and oxygen) using titanium tetrachloride as a raw material. The vapor-phase-produced titanium oxide has a uniform particle size and high crystallinity, attained by high-temperature processing. As a result, the thus-produced Cu- and Ti-containing composition exhibits excellent anti-viral property under light and in the dark, excellent organic compound degradability, and excellent anti-bacterial property.

In a preferred mode, a commercial product of titanium oxide is used as is, in consideration of catalyst preparation. Commercial titanium oxide products are produced through a liquid phase method or a vapor phase method. The liquid-phase-produced titanium oxide has a large specific surface area and a small rutile crystallinity. Therefore, the crystallinity and specific surface area of titanium oxide must be optimized through firing or a similar technique. However, such a process is cumbersome and elevates cost. In addition, undesired discoloration may occur during firing. From these viewpoints, preferred is use of a commercial titanium oxide produced through a vapor phase method having suitable crystallinity and specific surface area (e.g., rutile-type titanium oxide, product of SHOWA TITANIUM CO., LTD)

<Copper Compound>

The copper compound of the invention must be a divalent copper compound represented by the following formula (1):

$$Cu_2(OH)_3X \quad (1)$$

(wherein X represents an anion).

Although the divalent copper compound represented by formula (1) is a divalent copper compound, the compound exhibits anti-viral performance under the specific condition where it is used in combination with titanium oxide having a rutile-type titanium oxide content of 15 mol % or more. Thus, the composition containing the divalent copper compound exhibits excellent anti-viral property under light and in the dark, excellent organic compound degradability, and excellent anti-bacterial property. In addition, since the copper compound has divalent copper nature, time-dependent degradation in the above properties, which would otherwise be caused by oxidation or other phenomena, can be suppressed. Thus, the divalent copper compound must be used in combination with rutile-type titanium oxide.

In formula (1), X represents an anion, which is preferably a halogen such as Cl, Br, or I; an conjugate base such as $CH_3COO$, $NO_3$, or $(SO_4)_{1/2}$; or OH, more preferably Cl or $CH_3COO$.

The divalent copper compound represented by formula (1) may be a single-species divalent copper compound (i.e., a single divalent copper compound wherein X is a specific single component), or may be a mixture of two or more divalent copper compounds, for example, a mixture of $Cu_2(OH)_3(NO_3)$ and $Cu(OH)_2$.

The divalent copper compound represented by formula (1) may be in the form of anhydrate or hydrate.

The amount of the divalent copper compound represented by formula (1), as reduced to copper, is preferably 0.01 to 10 parts by mass, with respect to 100 parts by mass of the titanium oxide. When the divalent copper compound content is 0.01 parts by mass or more, anti-viral property, organic compound degradability, and anti-bacterial property are favorable, whereas when the content is 10 parts by mass or less, coverage of the surfaces of titanium oxide particles is prevented, to thereby effectively attain photocatalyst functions (organic compound degradability, anti-bacterial property, etc.). In this case, anti-viral performance can be enhanced by a small amount of divalent copper compound, which is economically advantageous. From this viewpoint, the amount of the divalent copper compound represented by formula (1), as reduced to copper, is more preferably 0.1 to 5 parts by mass, still more preferably 0.3 to 3 parts by mass, with respect to 100 parts by mass of titanium oxide.

The divalent copper compound content, as reduced to copper and with respect to 100 parts by mass of the titanium oxide may be calculated from the amount of fed divalent copper compound raw material and the amount of fed titanium oxide raw material. Alternatively, the content, as reduced to copper, may be determined by analyzing the Cu- and Ti-containing composition through the below-mentioned ICP (inductively coupled plasma) emission spectrophotometry.

As described above, the Cu- and Ti-containing composition of the present invention contains, as essential components, titanium oxide having a rutile-type titanium oxide content of 15 mol % or more, and at least one divalent copper compounds represented by formula (1). However, the composition of the invention may optionally contain another component, so long as the object of the present invention is not impeded. In order to enhance photocatalyst functions and anti-viral performance, the essential component content of the Cu- and Ti-containing composition is preferably 90 mass % or more, more preferably 95 mass % or more, still more preferably 99 mass % or more, yet more preferably 100 mass %.

[Method of Producing Cu- and Ti-Containing Composition]

No particular limitation is imposed on the method of producing Cu- and Ti-containing composition. Some preferred embodiments of the production method will be described.

<Production Example 1>

In Production Example 1, a mixture containing titanium oxide having a rutile-type titanium oxide content of 15 mol % or more, at least one divalent copper compound raw material represented by formula (2):

$$CuX_2 \quad (2)$$

(wherein X represents an anion), water, and an alkaline compound, is stirred to thereby cause precipitation.

Through the above procedure, the divalent copper compound raw material is hydrolyzed to form the divalent copper compound represented by the aforementioned formula (1) according to the following reaction scheme. Then, the compound is deposited on the surfaces of titanium oxide particles, whereby the aforementioned Cu- and Ti-containing composition is produced.

$$2CuX_2+TiO_2+3H_2O \rightarrow Cu_2(OH)_3X/TiO_2+3HX$$

In the reaction, "$Cu_2(OH)_3X/TiO_2$" refers to a state in which $Cu_2(OH)_3X$ is deposited on $TiO_2$.

(Titanium Oxide)

As the titanium oxide of the invention, the aforementioned titanium oxide having a rutile ratio of 15 mol % or more is used. In the above reaction, the above mixture preferably has a titanium oxide concentration of 3 to 25 mass %. When the concentration is 3 mass % or more, productivity is excellent, whereas when the concentration is 25 mass % or less, the obtained liquid has low viscosity, thereby facilitating handling of the mixture. Both cases are preferred.

(Divalent Copper Compound Raw Material Represented by Formula (2))

X in formula (2) is the same anion as that represented by X in formula (1). Thus, X is preferably a halogen such as Cl, Br, or I; an conjugate base such as $CH_3COO$, $NO_3$, or $(SO_4)_{1/2}$; or OH, more preferably Cl or $CH_3COO$.

The divalent copper compound raw material represented by formula (2) may be a single-species divalent copper compound raw material (i.e., a single divalent copper compound raw material wherein X is a specific single component), or may be a mixture of two or more divalent copper compound raw materials which have different Xs and are different from one another; e.g., a mixture of $Cu(NO_3)_2$ and $Cu(OH)_2$. Alternatively, the divalent copper compound raw material represented by formula (2) may be $CuX^1X^2$ (wherein $X^1$ and $X^2$ are anions different from each other).

The divalent copper compound raw material represented by formula (2) may be in the form of anhydrate or hydrate.
(Alkaline Compound)

Examples of the alkaline compound include sodium hydroxide, potassium hydroxide, tetramethylammonium hydroxide, tetrabutylammonium hydroxide, triethylamine, trimethylamine, ammonia, and a basic surfactant (e.g., BYK-9077, product of BYK Japan K.K.). Of these, sodium hydroxide is preferred.

The alkaline compound concentration of the solution to be added is preferably 0.1 to 5 mol/L, more preferably 0.3 to 4 mol/L, still more preferably 0.5 to 3 mol/L. A concentration of 5 mol/L or less is preferred, since uniform deposition can be realized upon addition of the alkaline compound.
(Solvent)

Water is used as a solvent. However, the solvent may further contain a polar solvent other than water, so long as $CuX_2$, water, an alkaline compound, which are raw materials, can be dissolved in the solvent. Examples of the polar solvent include an alcohol, a ketone, and a mixture thereof. Examples of the alcohol include methanol, ethanol, 1-propanol, 2-propanol, and 1-butanol. Examples of other polar solvents include dimethylformamide, tetrahydrofuran, and a mixture thereof.
(Mixing and Stirring)

No particular limitation is imposed on the order of mixing and stirring of titanium oxide, a divalent copper compound raw material, water, and an alkaline compound. In one preferred mode, titanium oxide is mixed with water optionally under stirring, and then the divalent copper compound raw material is added to the mixture under stirring. In an alternative mode, the divalent copper compound raw material is mixed with water optionally under stirring, and then titanium oxide is added to the mixture under stirring. In another alternative mode, the divalent copper compound raw material and titanium oxide are simultaneously added to water, and the mixture is stirred.

The alkaline compound may be added before, during, and/or after mixing of titanium oxide and/or the copper compound raw material with water. However, preferably, the alkaline compound is added after addition of titanium oxide and the divalent copper compound raw material to water, and sufficient mixing and stirring the mixture.

No particular limitation is imposed on the stirring time, and the stirring time is, for example, 5 to 120 minutes, preferably 10 to 60 minutes. No particular limitation is imposed on the temperature at which stirring is performed, and the temperature is, for example, room temperature to 70° C.

The mixture of titanium oxide, a divalent copper compound raw material, and water is preferably stirred at a pH of 8 to 11, when the stirring is performed at the reaction temperature. When the pH is 8 to 11, the divalent copper compound raw material is effectively hydrolyzed, whereby copper is deposited on the titanium oxide surface. In addition, the amount of alkaline compound used is reduced, making waste water treatment easy. From this viewpoint, the pH is more preferably 9 to 11, still more preferably 9.5 to 10.5. The pH is measured by means of a pH meter.
(Separation of Formed Cu- and Ti-Containing Composition)

The thus-produced Cu- and Ti-containing composition may be isolated as a solid from the liquid mixture. No particular limitation is imposed on the separation method, and examples of the method include filtration, sedimentation, centrifugation, and evaporation to dryness. Of these, separation by filtration is preferred.

If required, the thus-isolated Cu- and Ti-containing composition is subjected to washing with water, drying, pulverization, classification, etc.

<Production Example 2>

In Production Example 2, a raw material containing titanium oxide having a rutile-type titanium oxide content of 15 mol % or more, and at least one divalent copper compound represented by the aforementioned formula (1) is mixed, to thereby yield the aforementioned Cu- and Ti-containing composition.

Mixing may be carried out under dry or wet conditions. In the case of wet mixing, examples of the solvent include water, an alcohol, a ketone, and a mixture thereof. Examples of the alcohol include methanol, ethanol, 1-propanol, 2-propanol, 1-butanol, and a mixture thereof. Examples of the ketone include acetone, acetylacetone, methyl ethyl ketone, and a mixture thereof.

If required, the Cu- and Ti-containing composition produced through mixing is subjected to washing with water, drying, pulverization, classification, etc.
[Anti-Viral Agent and Photocatalyst]

The aforementioned Cu- and Ti-containing composition may be used as an anti-viral agent or a photocatalyst, since the composition has an anti-viral property under light and in the dark, an organic compound degradability (particularly visible-light-response), and an anti-bacterial property.
[Modes of Use of Cu- and Ti-Containing Composition, Anti-Viral Agent, and Photocatalyst]

No particular limitation is imposed on the mode of use of the Cu- and Ti-containing composition, anti-viral agent, and photocatalyst of the present invention (hereinafter these may be referred to as "the Cu- and Ti-containing composition or the like of the present invention"). In one mode thereof, the composition in the solid form, such as micropowder or granules, is directly charged into an appropriate container for use. In an alternative mode, the Cu- and Ti-containing composition or the like of the present invention is incorporated into the surface and/or the inside of a substrate. Generally, the latter mode is preferred.

No particular limitation is imposed on the substrate, and examples of the substrate include a substrate formed of a single member such as metal, ceramic material, glass, etc., and a composite substrate formed of two or more members. Alternatively, the Cu- and Ti-containing composition or the like of the present invention may be incorporated into a coating agent removable by appropriate means such as a floor polish. Yet alternatively, the Cu- and Ti-containing composition or the like of the present invention is immobilized on a membrane, to thereby realize a continuous membrane on which the Cu- and Ti-containing composition or the like of the present invention is exposed to the atmosphere. Still alternatively, a thin film of the Cu- and Ti-containing composition or the like of the present invention is formed through sputtering on a titanium oxide-sputtered glass thin film.

One typical example of the material including a substrate, and the Cu- and Ti-containing composition or the like of the present invention immobilized on the substrate is a material including the Cu- and Ti-containing composition or the like of the present invention immobilized on a substrate by immobilization means such as a binder. The binder may be an organic binder or an inorganic binder. Of these, an inorganic binder is preferably used, for the purpose of preventing decomposition of the binder induced by a photocatalytic substance. No particular limitation is imposed on the type of the binder, any binder may be used. Examples of the binder include an inorganic binder such as a silica-based binder, which is generally used for immobilizing a photocatalytic substance onto a substrate, and a polymer binder, which can form thin film through polymerization or vaporization of solvent.

One example of a material containing the Cu- and Ti-containing composition or the like of the present invention in the substrate thereof is a material produced by hardening a resin dispersion in which the Cu- and Ti-containing composition or the like of the present invention is dispersed. Either natural resin or synthetic resin may be used. No particular limitation is imposed on the type of resin, and examples of the resin include acrylic resin, phenolic resin, polyurethane resin, acrylonitrile-styrene copolymer resin, acrylonitrile-butadiene-styrene copolymer (ABS) resin, polyester resin, and epoxy resin.

No particular limitation is imposed on the mode of use of the Cu- and Ti-containing composition or the like of the present invention, and it may be used in the presence of any light beam or in the dark. The Cu- and Ti-containing composition or the like of the present invention, which exhibits high virus-inactivating performance in the presence of water (e.g., water or sea water), under dry conditions (e.g., low-humidity conditions in, for example, winter), under high humidity conditions, or in the co-presence of organic substance, can continuously inactivate viruses. The Cu- and Ti-containing composition or the like of the present invention may be applied to any object such as a wall, floor, or ceiling; buildings such as hospitals and factories; machine tools and measuring apparatuses; inside and parts of electric appliances (inside of a refrigerator, a cloth washer, a dish washer, etc., and a filter of an air purifier). Examples of preferred dark places include the inside a machine, a storage room of a refrigerator, a hospital facility (e.g., waiting room or surgical operation room), which is dark at night or when in a stand-by state. However, the object to which the Cu- and Ti-containing composition or the like of the present invention is applied is not particularly limited thereto. Meanwhile, there has been proposed a device having a titanium-oxide-coated ceramic or non-woven fabric filter employed in an air purifier, in combination with a light source for UV radiation, as one countermeasure against influenza. When the Cu- and Ti-containing composition or the like of the present invention is applied to such a filter, a UV light source may be omitted, thereby enhancing safety without elevating cost.

The present invention also provides a method for inactivating a virus or deodorizing by use of the aforementioned Cu- and Ti-containing composition.

EXAMPLES

The present invention will next be described in detail by way of examples, which should not be construed as limiting the invention thereto.

<Titanium Oxide Raw Materials>

The properties of titanium oxide raw materials employed in the Examples and the Comparative Examples were determined by the following procedures.

(BET Specific Surface Area)

The BET specific surface area of each titanium oxide raw material was measured by means of a full-automatic BET specific surface area measuring apparatus, "Macsorb HM, model-1208," which is a product of Mountech Co., Ltd.

(Rutile Content of Titanium Oxide Raw Material)

The rutile-type titanium oxide content of each titanium oxide raw material was determined through powder X-ray diffractometry.

Specifically, a dry titanium oxide raw material was analyzed through X-ray diffractometry by means of a diffractometer "X'pertPRO," which is a product of PANalytical, with a copper target for generating the Cu-Kα1 line. Measurement conditions included a tube voltage of 45 kV, a tube current of 40 mA, a measurement range 2θ=20 to 100°, a sampling width of 0.0167°, and a scanning speed of 1.1°/min.

The peak heights of maximum peaks corresponding to rutile-type crystal (Hr), brookite-type crystal (Hb), and anatase-type crystal (Ha) were measured, and the rutile-type titanium oxide content (rutile ratio) of titanium oxide was determined by the following calculation formula:

Rutile ratio (mol %) = $\{Hr/(Ha+Hb+Hr)\} \times 100$.

(Primary Particle Size)

Mean primary particle size ($D_{BET}$) (nm) was determined by measuring the specific surface area S (m$^2$/g) of titanium oxide through the BET single point method and by use of the following equation:

$$D_{BET} = 6000/(S \times \rho)$$

wherein $\rho$ represents the density (g/cm$^3$) of titanium oxide. Table 1 shows the measurement results of titanium oxide raw materials employed in the Examples, Comparative Examples, and other experiments.

TABLE 1

| | Type of titanium oxide | | | | | |
| --- | --- | --- | --- | --- | --- | --- |
| | A | B | C | D | E | Al$_2$O$_3$ |
| BET (m$^2$/g) | 10 | 20 | 20 | 100 | 150 | — |
| Rutile ratio (mol %) | 95.9 | 94.0 | 19.8 | 9.7 | 0 | — |
| Primary particle size (nm) | 150 | 75 | 75 | 15 | 10 | 50 |

Example 1

6 g (100 parts by mass) Of rutile-type titanium oxide A (product of SHOWA TITANIUM CO., LTD) was suspended in 100 mL of distilled water, and 0.0818 g (0.5 parts by mass as reduced to copper) of CuCl$_2$.2H$_2$O (product of Kanto Chemical Co., Inc.) was added to the suspension, followed by stirring for 10 minutes. Then, 1-mol/L aqueous solution of sodium hydroxide (product of Kanto Chemical Co., Inc.) was added to the mixture such that pH was adjusted to 10, and the resultant mixture was stirred for 30 minutes, to thereby form a slurry. The slurry was filtered, and the recovered powder was washed with pure water, dried at 80° C., and crushed by means of a mixer, to thereby prepare a sample.

The thus-obtained sample was dissolved in hydrofluoric acid, and the solution was heated to complete dissolution. An extract of the solution was analyzed through ICP emission spectrophotometry for quantitation. As a result, 0.5 parts by mass of copper ions were deposited on 100 parts by mass of titanium oxide particles. That is, the entire amount of fed copper ions (originating from CuCl$_2$.2H$_2$O) was found to be deposited on the titanium oxide surface.

Example 2

The procedure of Example 1 was repeated, except that rutile-type titanium oxide B (product of SHOWA TITANIUM CO., LTD) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 3

The procedure of Example 1 was repeated, except that rutile-type titanium oxide C (product of SHOWA TITANIUM CO., LTD) was used instead of rutile-type titanium oxide A (product of SHOWA TITANIUM CO., LTD), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 4

The procedure of Example 1 was repeated, except that 0.0952 g (0.5 parts by mass as reduced to copper) of $Cu(CH_3COO)_2 \cdot H_2O$ (product of Kanto Chemical Co., Inc.) was used instead of 0.0818 g (0.5 parts by mass as reduced to copper) of $CuCl_2 \cdot 2H_2O$ (product of Kanto Chemical Co., Inc.), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 5

The procedure of Example 1 was repeated, except that 0.1187 g (0.5 parts by mass as reduced to copper) of $CuSO_4 \cdot 5H_2O$ (product of Kanto Chemical Co., Inc.) was used instead of 0.0818 g (0.5 parts by mass as reduced to copper) of $CuCl_2 \cdot 2H_2O$ (product of Kanto Chemical Co., Inc.), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 6

The procedure of Example 1 was repeated, except that 0.1154 g (0.5 parts by mass as reduced to copper) of $Cu(NO_3)_2 \cdot 3H_2O$ (product of Kanto Chemical Co., Inc.) was used instead of 0.0818 g (0.5 parts by mass as reduced to copper) of $CuCl_2 \cdot 2H_2O$ (product of Kanto Chemical Co., Inc.), to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Example 7

The procedure of Example 1 was repeated, except that the amount of $CuCl_2 \cdot 2H_2O$ (product of Kanto Chemical Co., Inc.) was changed to 0.0163 g (0.1 parts by mass as reduced to copper), to thereby produce a sample.

The sample was analyzed through ICP emission spectrophotometry in a manner similar to that of Example 1. As a result, 0.1 parts by mass of copper ions were deposited on 100 parts by mass of titanium oxide particles. That is, the entire amount of fed copper ions was found to be deposited on the titanium oxide surface.

Example 8

The procedure of Example 1 was repeated, except that the amount of $CuCl_2 \cdot 2H_2O$ (product of Kanto Chemical Co., Inc.) was changed to 0.818 g (5 parts by mass as reduced to copper), to thereby produce a sample.

The sample was analyzed through ICP emission spectrophotometry in a manner similar to that of Example 1. As a result, 5 parts by mass of copper ions were deposited on 100 parts by mass of titanium oxide particles. That is, the entire amount of fed copper ions was found to be deposited on the titanium oxide surface.

Also, the sample was pulverized by means of a mortar, and the powder was analyzed through X-ray diffractometry by means of a diffractometer "X'pertPRO," which is a product of PANalytical, with a copper target for generating the Cu-K$\alpha$1 line. Measurement conditions included a tube voltage of 45 kV, a tube current of 40 mA, a measurement range 2$\theta$=20 to 100°, a sampling width of 0.0167°, and a scanning speed of 1.1°/min. With reference to a database included in the above apparatus, a peak attributed to $Cu_2(OH)_3Cl$ was identified.

Comparative Example 1

The procedure of Example 1 was repeated, except that anatase-type titanium oxide D (product of SHOWA TITANIUM CO., LTD) was used instead of rutile-type titanium oxide A, to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Comparative Example 2

The procedure of Example 1 was repeated, except that brookite-type titanium oxide E (product of SHOWA TITANIUM CO., LTD) was used instead of rutile-type titanium oxide A, to thereby produce a sample.

The sample was analyzed through ICP emission spectrophotometry in a manner similar to that of Example 1. As a result, 0.5 parts by mass of copper ions were deposited on 100 parts by mass of titanium oxide particles. That is, the entire amount of fed copper ions was found to be deposited on the titanium oxide surface.

Comparative Example 3

The procedure of Example 1 was repeated, except that aluminum oxide ($Al_2O_3$, product of Aldrich) was used instead of rutile-type titanium oxide A, to thereby produce a sample.

The sample was analyzed through ICP emission spectrophotometry in a manner similar to that of Example 1. As a result, 0.5 parts by mass of copper ions were deposited on 100 parts by mass of aluminum oxide particles. That is, the entire amount of fed copper ions was found to be deposited on the aluminum oxide surface.

Comparative Example 4

Rutile-type titanium oxide A (product of SHOWA TITANIUM CO., LTD) was used as a sample.

Comparative Example 5

3 g of $CuCl_2 \cdot 2H_2O$ (product of Kanto Chemical Co., Inc.) was suspended in 100 mL of distilled water, and the suspension was stirred for 10 minutes. Then, 1-mol/L aqueous solution of sodium hydroxide (product of Kanto Chemical Co., Inc.) was added to the suspension such that pH was adjusted to 10, and the resultant mixture was stirred for 30 minutes, to thereby form a slurry. The slurry was filtered, and the recovered powder was washed with pure water, dried at 80° C., and crushed by means of a mixer, to thereby yield single-phase $Cu_2(OH)_3Cl$ as a sample.

Referential Example 1

6 g (100 parts by mass) Of rutile-type titanium oxide A (product of SHOWA TITANIUM CO., LTD) was suspended in 100 mL of distilled water, and 0.0818 g (0.5 parts by mass as reduced to copper) of $CuCl_2 \cdot 2H_2O$ (product of Kanto Chemical Co., Inc.) was added to the suspension, followed by stirring for 10 minutes. Then, 1-mol/L aqueous solution of sodium hydroxide (product of Kanto Chemical Co., Inc.) was added to the mixture such that pH was adjusted to 10. Then, 12.0 mL of 0.01-mol/L aqueous hydrazine (product of Kanto Chemical Co., Inc.) was added to the mixture, so that the ratio by mole $CuCl_2 \cdot 2H_2O:N_2H_4$ was adjusted to 1:0.25, and the resultant mixture was stirred for 30 minutes, to thereby form a slurry. The slurry was filtered, and the recovered powder was washed with pure water, dried at 80° C., and crushed by means of a mixer, to thereby prepare a sample.

The thus-obtained sample was dissolved in hydrofluoric acid, and the solution was heated to complete dissolution. An extract of the solution was analyzed through ICP emission spectrophotometry for quantitation. As a result, 0.5 parts by mass of copper ions were deposited on 100 parts by mass of titanium oxide particles. That is, the entire amount of fed copper ions (originating from $CuCl_2 \cdot 2H_2O$) was found to be deposited on the titanium oxide surface.

<Measurement>
(Evaluation of Anti-Viral Performance Under Light: Determination of $LOG(N/N_0)$)

The anti-viral performance of the samples was assessed through the following model experiment employing bacteriophage. Notably, assessment of anti-viral performance with respect to inactivation performance with respect to bacteriophage is disclosed in, for example, Appl. Microbiol. Biotechnol., 79, pp. 127-133, 2008. The bacteriophage inactivation performance is known as a reliable model for the assessment.

A filter paper piece was placed on the bottom of a deep Petri dish, and a small amount of sterilized water was added to the Petri dish. A glass base plate having a thickness of about 5 mm was placed on the filter paper piece. On the glass base plate, there was placed a glass plate (50 mm×50 mm×1 mm) onto which each of the samples of the Examples and the Comparative Examples in an amount of 5 mg had been applied. 100 μL of QBphage (NBRC20012) suspension which had been purified in advance and whose concentration had been determined was added dropwise to the glass plate. In order to bring the sample surface into contact with the phage, the glass plate was covered with OHP film made of PET (polyethylene terephthalate). A glass lid was put on the deep Petri dish, to thereby provide a measurement unit. Regarding each sample, a plurality of measurement units were provided.

A 15 W white fluorescent lamp (Full white fluorescent lamp, FL15N, product of Panasonic Corporation) equipped with a UV-cutting filter (KU-1000100, product of King Works Co., Ltd.) was employed as a light source. The aforementioned measurement units were placed under the light source at a position where the illuminance (measured by means of an illuminometer: TOPCON IM-5) was 800 lx. After the elapse of a predetermined time, the phage concentration of each sample present on the glass plate was measured.

Phage concentration was determined through the following procedure. The sample present on the glass plate was recovered with 10 mL of a phage recovery liquid (SM Buffer), and the liquid was shaken by means of a shaker for 10 minutes. The phage-recovered liquid was appropriately diluted, and the dilution was mixed with a separately prepared E. coli (NBRC 13965) culture liquid ($OD_{600}>1.0$, $1 \times 10^8$ CFU/mL) under stirring. Thereafter, the mixture was allowed to stand in a thermostat container at 37° C. for 10 minutes, to thereby infect E. coli with the phage. The resultant liquid was added to an agar medium, and culturing was performed at 37° C. for 15 hours. The number of plaques of the phage was visually counted. The phage concentration N was derived through multiplication of the count by the dilution factor of the phage-recovered liquid.

From the initial phage concentration $N_0$ and phage concentrations N after the elapse of a predetermined time, the relative phage concentration ($LOG(N/N_0)$) was determined. Table 2 and FIG. 1 show the results.

(Evaluation of Anti-Viral Performance in the Dark: Determination of $LOG(N/N_0)$)

Figure 2:
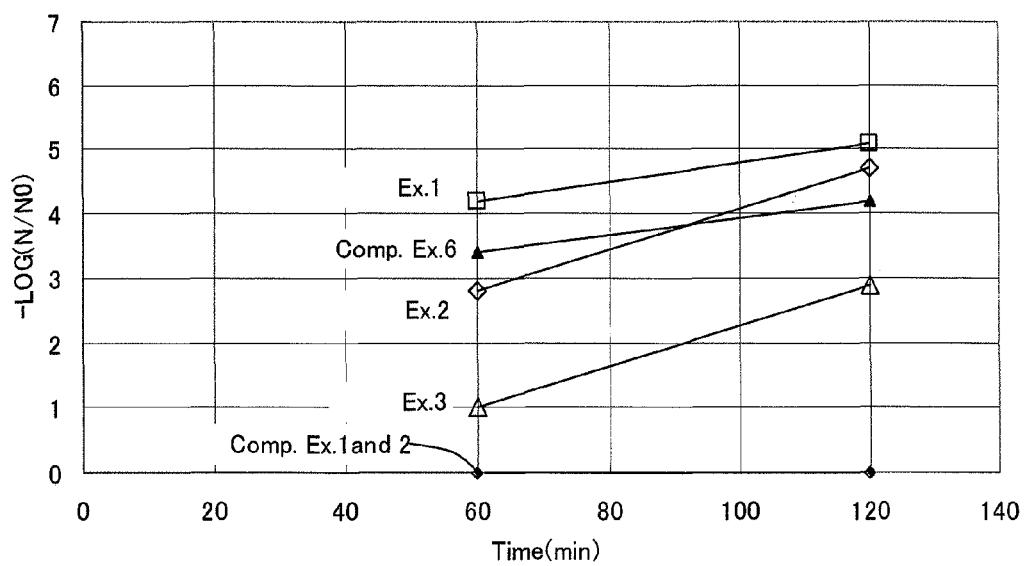
FIG. 2 A graph showing changes over time in relative phage concentration (LOG(N/N₀)) of samples of Examples 1 to 3 and Comparative Examples 1, 2, and 6, in the dark.

The procedure of "Evaluation of anti-viral performance under light: determination of $LOG(N/N_0)$" was repeated, except that measurement units were placed in the dark without irradiation with light from the light source. Table 2 and FIG. 2 show the results.

(Evaluation of Volatile Organic Compound (VOC) Decomposition Activity Under Light: Measurement of $CO_2$ Generation Amount)

In a sealable glass reactor (capacity: 0.5 L), glass Petri dishes each having a diameter of 1.5 cm were placed. On each Petri dish, 0.1 g of each of the samples produced in the Examples and the Comparative Examples was placed. The atmosphere inside the reactor was substituted by a mixture of oxygen and nitrogen with a volume ratio of 1:4. To the reactor, 5.2 μL of water (corresponding to a relative humidity of 50% (25° C.)), and 5.0 mL of 5.1 vol. % acetaldehyde standard gas (mixture with nitrogen, standard temperature and pressure (25° C., 1 atm)) were added, and the reactor was closed (acetaldehyde concentration in the glass reactor adjusted to 500 ppm by volume). The reactor was irradiated with visible light.

Irradiation with visible light was carried out by means of a light source including a xenon lamp equipped with a filter which cuts UV rays having a wavelength of 400 nm or shorter (trade name: L-42, AGC Techno Glass Co., Ltd.). The light source was set so that the illuminance in the reactor was adjusted to 100,000 lx. The rate of decrease of acetaldehyde, and the rate of generation of carbon dioxide, which is a decomposition product via oxidation, were monitored through gas chromatography. Table 2 shows the $CO_2$ generation amount (ppm by mass) 3 hours after a start of irradiation with visible light.

pound represented by formula (1), exhibited no anti-viral property under light or in the dark, or no VOC decomposition activity.

The sample of Comparative Example 4, which was single-phase rutile-type titanium oxide, exhibited no anti-viral property under light or in the dark.

The sample of Comparative Example 5, which was a single-phase compound represented by formula (1), exhibited no anti-viral property under light or in the dark, or no VOC decomposition activity.

The invention claimed is:

1. A Cu- and Ti-containing composition which inhibits vital growth when applied to a substrate, or when added to a medium, in a virtually-inhibiting effective amount, comprising titanium oxide having a rutile-type titanium oxide content of 50 mol % or more, and at least one divalent copper compound represented by the following formula (1):

$$Cu_2(OH)_3X \quad (1)$$

(wherein X represents an anion),
and the composition has a copper content, as reduced to elemental copper, of at least 0.5 parts by mass, with respect to 100 parts by mass of titanium dioxide;

TABLE 2

| | Ti oxide or Al oxide | | | Cu compd. or Cu metal | | | Anti-viral property (light) −LOG (N/N0) [/min irradn.] | | | Anti-viral property (dark) −LOG (N/N0) [/min irradn.] | | VOC decompn. activity $CO_2$ generation (3 h) [/ppm] |
|---|---|---|---|---|---|---|---|---|---|---|---|---|
| | Type | Rutile ratio (mol/%) | Parts by mass | Type | Cu parts by mass | Deposit or single phase | 30 | 60 | 120 | 60 | 120 | Under light |
| Ex. 1 | A | 95.9 | 100 | $Cu_2(OH)_3Cl$ | 0.5 | deposit | 3.5 | 5.6 | 6.6 | 4.2 | 5.1 | 144 |
| Ex. 2 | B | 94.0 | 100 | $Cu_2(OH)_3Cl$ | 0.5 | deposit | 4.5 | 4.9 | 5.6 | 2.8 | 4.7 | 202 |
| Ex. 3 | C | 19.8 | 100 | $Cu_2(OH)_3Cl$ | 0.5 | deposit | 2.8 | 3.8 | 3.9 | 1.0 | 2.9 | 136 |
| Ex. 4 | A | 95.9 | 100 | $Cu_2(OH)_3(CH_3COO)$ | 0.5 | deposit | 3.4 | 6.9 | 6.9 | 3.9 | 5.2 | 103 |
| Ex. 5 | A | 95.9 | 100 | $Cu_2(OH)_3(SO_4)_{1/2}$ | 0.5 | deposit | 5.9 | 6.9 | 6.9 | 4.5 | 4.0 | 105 |
| Ex. 6 | A | 95.9 | 100 | $Cu_2(OH)_3(NO_3)$ | 0.5 | deposit | 5.7 | 5.6 | 5.5 | 3.2 | 3.6 | 102 |
| Ex. 7 | A | 95.9 | 100 | $Cu_2(OH)_3Cl$ | 0.1 | deposit | 1.3 | 1.8 | 2.6 | 1.5 | 1.3 | 318 |
| Ex. 8 | A | 95.9 | 100 | $Cu_2(OH)_3Cl$ | 5 | deposit | 4.1 | 6.9 | 6.9 | 4.6 | 6.6 | 169 |
| Comp. Ex. 1 | D | 9.7 | 100 | $Cu_2(OH)_3Cl$ | 0.5 | deposit | 0.1 | 0.1 | 0.1 | 0.0 | 0.0 | 102 |
| Comp. Ex. 2 | E | 0 | 100 | $Cu_2(OH)_3Cl$ | 0.5 | deposit | 0.0 | 0.0 | 0.0 | 0.0 | 0.0 | 112 |
| Comp. Ex. 3 | $Al_2O_3$ | — | 100 | $Cu_2(OH)_3Cl$ | 0.5 | deposit | 0.0 | 0.3 | 0.7 | 0.3 | 0.3 | 0 |
| Comp. Ex. 4 | A | 95.9 | 100 | — | — | single phase | 0.1 | 0.6 | 1.2 | 0.0 | 0.1 | 205 |
| Comp. Ex. 5 | — | — | — | $Cu_2(OH)_3Cl$ | 100 | single phase | 0.0 | 0.0 | 0.0 | 0.0 | 0.0 | 0 |
| Ref. Ex. 1 | A | 95.9 | 100 | $Cu_2O$ | 0.5 | deposit | 2.4 | 4.6 | 5.9 | 3.4 | 4.2 | 138 |

<Results>

The samples of Examples 1 to 8 exhibited excellent anti-viral property under light and in the dark as well as excellent VOC decomposition activity.

Notably, the samples of Examples 1 and 4 to 6, and Referential Example 1 were formed of the same rutile-type titanium oxide on which the same amount (0.5 parts by mass) of a compound represented by formula (1) (Examples 1 and 4 to 6) or a monovalent copper oxide (referential Example 1) was deposited. Through comparison, a composition containing a divalent copper compound represented by formula (1) and rutile-type titanium oxide exhibited anti-viral property under light and in the dark as well as excellent VOC decomposition activity, which were equivalent to or superior to those of a composition containing a monovalent copper compound and rutile-type titanium oxide.

In contrast, the samples of Comparative Examples 1 and 2, having a rutile ratio lower than the lower limit of the present invention (15 mol %), exhibited substantially no anti-viral property under light or in the dark.

The sample of Comparative Example 3, which contained alumina instead of rutile-type titanium oxide, and a comwherein the total content of the titanium oxide and the at least one divalent copper compound is 90 mass % or more.

2. The Cu- and Ti-containing composition according to claim 1, wherein, in formula (1), X is Cl.

3. The Cu- and Ti-containing composition according to claim 1, wherein the divalent copper compound represented by formula (1) has a copper content, as reduced to copper, of 5 to 10 parts by mass, with respect to 100 parts by mass of titanium oxide.

4. The Cu- and Ti-containing composition according to claim 1, wherein the titanium oxide has been produced through a vapor phase method.

5. The Cu- and Ti-containing composition according to claim 1, wherein the titanium oxide has a specific surface area of 8 to 50 $m^2/g$.

6. The Cu- and Ti-containing composition of claim 1 which inhibits viral growth in the dark.

7. The Cu- and Ti- containing composition of claim 1, wherein the type of virus is bacteriophage.

8. The Cu- and Ti- containing composition of claim 1, wherein the copper is deposited on the surface of the titanium oxide.

9. A photocatalyst containing the Cu- and Ti- containing composition as recited in claim 1.

10. A method for producing a Cu- and Ti-containing composition as claimed in claim 1, characterized in that the method comprises stirring a mixture containing titanium oxide having a rutile-type titanium oxide content of 50 mol % or more, a divalent copper compound raw material represented by formula (2):

$$CuX_2 \quad (2)$$

(wherein X represents an anion), water, and an alkaline compound, to thereby cause precipitation.

11. The Cu- and Ti-containing composition production method according to claim 10, wherein the mixture is stirred at a pH of 8 to 11.

12. The Cu- and Ti-containing composition production method according to claim 10, wherein the mixture has a titanium oxide concentration of 3 to 25 mass %.

13. The Cu- and Ti-containing composition production method according to claim 10, wherein, in formula (2), X is Cl.

* * * * *